US 9,805,902 B2

(12) United States Patent
Simon et al.

(10) Patent No.: US 9,805,902 B2
(45) Date of Patent: Oct. 31, 2017

(54) ENERGY RADIATION GENERATOR WITH BI-POLAR VOLTAGE LADDER

(75) Inventors: Matthieu Simon, Houston, TX (US); Anthony Durkowski, Round Rock, TX (US); Christian Stoller, Princeton Junction, NJ (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 520 days.

(21) Appl. No.: 14/344,513

(22) PCT Filed: Sep. 14, 2012

(86) PCT No.: PCT/US2012/055478
§ 371 (c)(1),
(2), (4) Date: Oct. 27, 2014

(87) PCT Pub. No.: WO2013/040390
PCT Pub. Date: Mar. 21, 2013

(65) Prior Publication Data
US 2015/0055747 A1 Feb. 26, 2015

Related U.S. Application Data

(60) Provisional application No. 61/534,446, filed on Sep. 14, 2011.

(51) Int. Cl.
*H01J 35/02* (2006.01)
*H01J 37/06* (2006.01)
(Continued)

(52) U.S. Cl.
CPC .......... *H01J 35/025* (2013.01); *E21B 47/011* (2013.01); *E21B 47/082* (2013.01);
(Continued)

(58) Field of Classification Search
CPC ...... H01J 3/00; H01J 3/02; H01J 3/023; H01J 29/482; H01J 37/061; H01J 43/00;
(Continued)

(56) References Cited

U.S. PATENT DOCUMENTS 3,320,513 A   5/1967   Cleland
3,381,204 A   4/1968   Cox
(Continued)

FOREIGN PATENT DOCUMENTS

CN   2161722 Y   4/1994
CN   2591626 Y   12/2003
(Continued)

OTHER PUBLICATIONS

International Search Report for International Application No. PCT/US2012/055478 dated Feb. 25, 2013.
(Continued)

*Primary Examiner* — Anastasia Midkiff
(74) *Attorney, Agent, or Firm* — Michael Dae

(57) ABSTRACT

A well-logging tool may include a sonde housing, and a radiation generator carried by the sonde housing. The radiation generator may include a generator housing, a target carried by the generator housing, a charged particle source carried by the generator housing to direct charged particles at the target, and at least one voltage source coupled to the charged particle source. The at least one voltage source may include a voltage ladder comprising a plurality of voltage multiplication stages coupled in a bi-polar configuration, and at least one loading coil coupled at at least one intermediate position along the voltage ladder. The well-logging tool may further include at least one radiation detector carried by the sonde housing.

23 Claims, 10 Drawing Sheets

(51) Int. Cl.
| | |
|---|---|
| E21B 47/01 | (2012.01) |
| E21B 47/08 | (2012.01) |
| G01N 23/20 | (2006.01) |
| G01V 5/04 | (2006.01) |
| G01V 5/12 | (2006.01) |
| G01V 3/12 | (2006.01) |
| G01V 3/30 | (2006.01) |
| G01V 5/00 | (2006.01) |
| E21B 47/10 | (2012.01) |
| H05G 1/10 | (2006.01) |
| H01J 3/02 | (2006.01) |
| H01J 43/04 | (2006.01) |
| G01N 9/24 | (2006.01) |
| G01N 35/00 | (2006.01) |
| E21B 49/00 | (2006.01) |
| H02M 7/10 | (2006.01) |
| H05H 3/06 | (2006.01) |
| H05H 5/04 | (2006.01) |

(52) U.S. Cl.
CPC ... *E21B 47/1015* (2013.01); *G01N 23/20008* (2013.01); *G01V 3/12* (2013.01); *G01V 3/30* (2013.01); *G01V 5/0008* (2013.01); *G01V 5/04* (2013.01); *G01V 5/12* (2013.01); *H01J 37/061* (2013.01); *H05G 1/10* (2013.01); *E21B 49/00* (2013.01); *G01N 9/24* (2013.01); *G01N 2035/00306* (2013.01); *G01N 2201/0227* (2013.01); *G01N 2223/05* (2013.01); *G01N 2223/204* (2013.01); *G01N 2223/30* (2013.01); *H01J 3/023* (2013.01); *H01J 43/04* (2013.01); *H02M 7/103* (2013.01); *H05H 3/06* (2013.01); *H05H 5/045* (2013.01); *Y10T 29/41* (2015.01); *Y10T 29/49117* (2015.01)

(58) Field of Classification Search
CPC .. H01J 43/04; H01J 35/00; H01J 35/02; H01J 35/025; H01J 35/16; E21B 47/00; E21B 47/0006; E21B 47/01; E21B 47/011; E21B 47/02216; E21B 47/024; E21B 47/026; E21B 47/08; E21B 47/082; E21B 47/09; E21B 47/10; G01N 21/954; G01N 21/01; G01N 35/0099; G01N 2291/2636; G01N 2021/9542; G01N 2021/9544; G01N 2021/9548; G01N 2021/0106; G01N 9/24; G01N 2223/00; G01N 2223/05; G01N 2223/052; G01N 2223/053; G01N 2223/101; G01N 2223/1016; G01N 2223/30; G01N 2223/301; G01N 23/00; G01N 23/20; G01N 23/20008; G01N 23/203; G01N 2035/00178; G01N 2035/00188; G01N 2035/00306; G01N 2035/00326; G01N 2201/00; G01N 2201/02; G01N 2201/021; G01N 2201/022; G01N 2201/0227; G01N 2201/023; G01N 2201/024; G01V 1/40; G01V 1/44; G01V 1/46; G01V 1/52; G01V 2001/526; G01V 3/00; G01V 3/12; G01V 3/14; G01V 3/18; G01V 3/30; G01V 3/32; G01V 3/36; G01V 5/00; G01V 5/0008; G01V 5/04; G01V 5/045; G01V 5/08; G01V 5/10; G01V 5/12; G01V 5/14; G01V 11/00; G01V 11/002; G01V 11/005; G01V 13/00
See application file for complete search history.

(56) References Cited

U.S. PATENT DOCUMENTS

| | | | |
|---|---|---|---|
| 3,539,903 A | 11/1970 | Goebel | |
| 3,878,449 A * | 4/1975 | Wilhelmi | H03K 3/57 307/108 |
| 4,292,592 A | 9/1981 | Birdwell et al. | |
| 4,629,889 A | 12/1986 | Todokoro et al. | |
| 4,945,464 A * | 7/1990 | Gunn | H02M 7/10 363/61 |
| 5,231,564 A | 7/1993 | Pellegrino et al. | |
| 5,523,939 A | 6/1996 | Stephenson | |
| 5,680,431 A | 10/1997 | Pietras, III et al. | |
| 6,198,804 B1 | 3/2001 | Dinsmore | |
| 7,542,543 B2 | 6/2009 | Shampine et al. | |
| 7,564,948 B2 | 7/2009 | Wraight et al. | |
| 7,639,781 B2 | 12/2009 | Shampine et al. | |
| 9,091,777 B2 * | 7/2015 | Simon | G01V 5/12 |
| 2007/0237298 A1 * | 10/2007 | Sundaram | H05G 1/06 378/101 |
| 2008/0159480 A1 | 7/2008 | Wraight et al. | |
| 2010/0226156 A1 | 9/2010 | Hanington | |
| 2011/0002443 A1 | 1/2011 | Wraight et al. | |
| 2011/0114830 A1 | 5/2011 | Reijonen et al. | |
| 2011/0180698 A1 | 7/2011 | Stephenson | |
| 2013/0208841 A1 * | 8/2013 | Perkins | G21G 4/02 376/114 |

FOREIGN PATENT DOCUMENTS

| | | |
|---|---|---|
| CN | 1793607 A | 6/2006 |
| CN | 101191839 A | 6/2008 |
| CN | 101418684 A | 4/2009 |
| CN | 101421490 A | 4/2009 |
| CN | 101460003 A | 7/2009 |
| CN | 101845948 A | 9/2010 |
| CN | 104093932 A | 10/2014 |
| DE | 931540 C | 8/1955 |
| GB | 977528 A | 12/1964 |
| RU | 87555 U1 | 10/2009 |
| RU | 2399977 C1 | 9/2010 |
| WO | 2009099887 A1 | 8/2009 |
| WO | 2010090795 A1 | 8/2010 |
| WO | 2013040390 A2 | 3/2013 |
| WO | 2013040402 A2 | 3/2013 |

OTHER PUBLICATIONS

International Search Report for International Application No. PCT/US2012/055497 dated Feb. 27, 2013.
Office Action No. 21674 issued in related MX application MX/a/2014/003007 dated Mar. 22, 2016, 7 pages.
Office Action No. 21542 issued in related MX application MX/a/2014/003008 dated Mar. 22, 2016, 7 pages.
First Office Action issued in related CN application 201280055631.2 dated Apr. 20, 2016, 22 pages.
First Office Action issued in related CN application 201280055695.2 dated Jan. 27, 2016, 19 pages.
Iqbal et al., "A Bipolar Cockcroft-Walton Voltage Multiplier for Gas Lasers", Oct. 1, 2007, American Journal of Applied Sciences, vol. 4 No. 10, pp. 795-801.
European Search Report issued in EU application 12831724.5 dated May 4, 2015, 4 pages.
Office Action issued in EU application 12831724.5 dated May 26, 2015, 4 pages.
Supplementary European Search Report issued in EU application 12831724.5, 3 pages.
Office Action issued in corresponding Chinese application 201280055695.2 dated Sep. 30, 2016. English Translation included. 18 pages.
Search Report (R. 61 or R. 63 EPC) issued in related European Application 12831040.6 dated Apr. 30, 2015. 3 pages.
Examination Report 94(3) EPC in related European Application 12831040.6 dated May 26, 2015. 5 pages.

(56) References Cited

OTHER PUBLICATIONS

International Preliminary Report on Patentability issued in corresponding International application PCT/US2015/055478, 6 pages.
International Preliminary Report on Patentability issued in related International application PCT/US2015/055497, 8 pages.
Mexican Office Action No. 62720 issued in related MX application MX/a/2014/003007 dated Aug. 10, 2016, 12 pages.
Mexican Office Action No. 63062 issued in related MX application MX/a/2014/003007 dated Aug. 11, 2016, 10 pages.
Decision on Grant issued in related RU application 2014114049 dated Jun. 16, 2016, 18 pages.
Decision on Grant issued in related RU application 2014114526 dated Jun. 16, 2016, 18 pages.

* cited by examiner

ENERGY RADIATION GENERATOR WITH BI-POLAR VOLTAGE LADDER

BACKGROUND

Radiation generators, such as neutron and X-ray generators, are used in well logging tools to take measurements of a geological formation adjacent a wellbore where hydrocarbon resources may be located (e.g., oil and/or natural gas). Neutron generators may use deuterium-deuterium (d-d), deuterium-tritium (d-t) or tritium-tritium (t-t) reactions to create neutrons without the use of radioactive materials.

Radiation generators may include a tube (e.g., a neutron or X-ray tube) and associated electrical components, such as one or more high voltage transformers with a Cockcroft-Walton ladder to produce a high operating voltage. A neutron tube is a sealed envelope made of metal and insulators including a gas reservoir, an ion source, an accelerator column and a target. The target may be made of a hydride material. Once released from the reservoir, the gas is ionized in the ion source, and then accelerated in the accelerator column toward the target. A nuclear fusion reaction occurs between the incoming ions and the hydrogen isotope atoms present in the target, causing neutrons to be directed into the geological formation. A radiation detector may detect the radiation from the geological formation resulting from the neutron bombardment, which in turn provides information regarding the composition of the geological formation.

An X-ray tube has an electron source (often called an electron gun), an acceleration column and a target. The target may be made of a heavy material, such as tungsten or gold, for example.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A well-logging tool may include a sonde housing, and a radiation generator carried by the sonde housing. The radiation generator may include a generator housing, a target carried by the generator housing, a charged particle source carried by the generator housing to direct charged particles at the target, and at least one voltage source coupled to the charged particle source. The at least one voltage source may include a voltage ladder comprising a plurality of voltage multiplication stages coupled in a bi-polar configuration, and at least one loading coil coupled at at least one intermediate position along the voltage ladder. The well-logging tool may further include at least one radiation detector carried by the sonde housing.

A radiation generator may include a generator housing, a target carried by the generator housing, a charged particle source carried by the generator housing to direct charged particles at the target, and at least one voltage source coupled to the charged particle source. The at least one voltage source may include a voltage ladder comprising a plurality of voltage multiplication stages coupled in a bi-polar configuration, where each multiplication stage include at least one semiconductor diode. At least one loading coil may be coupled at at least one intermediate position along the voltage ladder.

A method for making a radiation generator may include positioning a target and a charged particle source in a generator housing so that the charged particle source directs charged particles at the target, and coupling at least one voltage source to the charged particle source. The at least one voltage source may include a voltage ladder comprising a plurality of voltage multiplication stages coupled in a bi-polar configuration, where each multiplication stage may include at least one semiconductor diode, and at least one loading coil coupled at at least one intermediate position along the voltage ladder.

DETAILED DESCRIPTION

The present description is made with reference to the accompanying drawings, in which example embodiments are shown. However, many different embodiments may be used, and thus the description should not be construed as limited to the embodiments set forth herein. Rather, these embodiments are provided so that this disclosure will be thorough and complete. Like numbers refer to like elements throughout, and prime and multiple prime notation are used to indicate similar elements in different embodiments.

Figure 1:
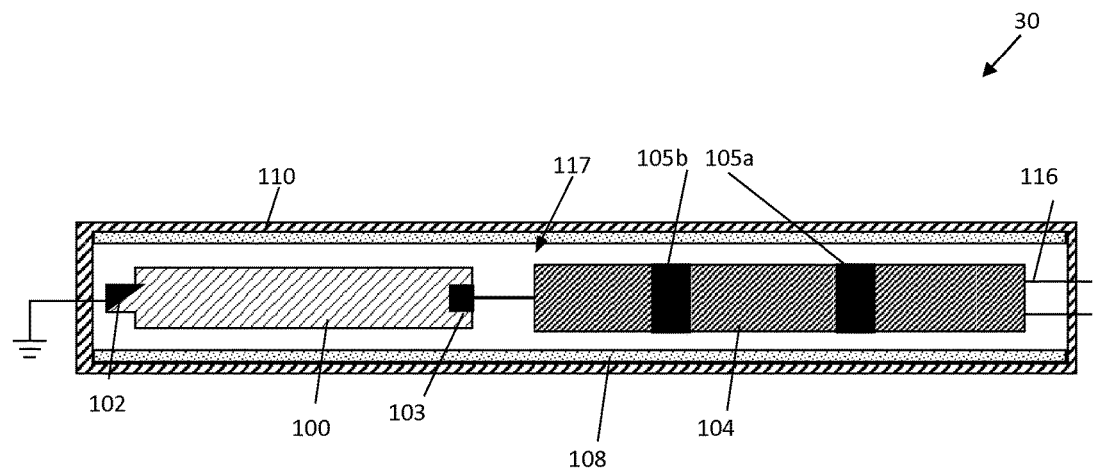
FIG. 1 is a cross-sectional side view of a radiation generator in accordance with an example embodiment.
Figure 2:
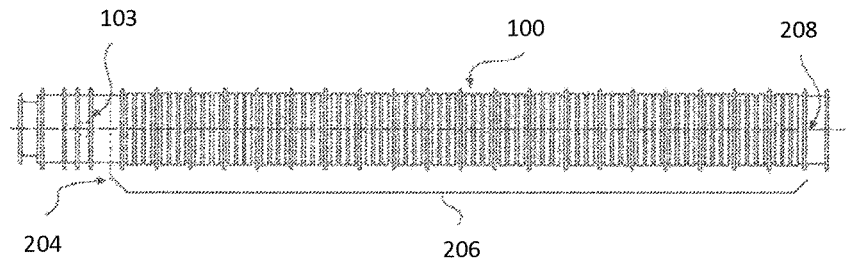
FIG. 2 is a side view of an X-ray tube which may be used in the radiation generator of FIG. 1 in an example embodiment.

Referring initially to FIGS. 1 and 2, a radiation generator 30 is first described. In the illustrated example, the radiation generator is an X-ray generator which includes an X-ray tube 100 that is grounded at a target (i.e., anode) end 102, although floating target configurations may also be used in some embodiments. The X-ray tube 100 further illustratively includes a cathode 103 on the opposite end of the tube from the target end 102. The cathode 103 is coupled to a voltage multiplication ladder 104 (e.g., via a cathode isolation transformer, for example). The X-ray tube 100, voltage multiplication ladder 104, and an isolation transformer 106 are enclosed within one or more insulating sleeves 108 (e.g., PFA), which in turn is enclosed within a generator housing 110. An insulating gas may be inserted in the inner space 117 within the generator housing. The voltage multiplication ladder 104 further illustratively includes a plurality of loading coils 105a, 105b, which will be described further below, and an input 116 for receiving an AC voltage. The grounded target configuration shown schematically in FIG. 1 provides a simplification in the mechanical design and assembly, which may also help in maintaining mechanical stability of the target, maintaining thermal management of the target, as well as the radiation exposure of the insulating material 108.

The cathode 103 releases electrons in response to exposure to heat, although in some embodiments "cold" cathodes (e.g., Carbon nanotubes, etc.) may also be used. As will be described further below, voltage ladder 104 applies a voltage to the cathode 103, and the introduction of current heats the cathode 103 and causes it to release electrons. A grid 204 moves electrons released from the cathode 103 toward an electron accelerating section 206. The accelerating section 206 speeds electrons toward a target 208. Upon collision with the target 208, X-rays are generated which may be used in various applications, such as downhole well-logging measurements, as will be discussed further below.

A basic uni-polar voltage ladder configuration may be inadequate for achieving very high voltages (e.g., on the order of hundreds of KeV) within the space confines dictated for downhole use. That is, given the space constraints of the downhole tool pad or sonde housing in which a voltage ladder is deployed, it may be difficult to achieve desired voltage levels with the basic uni-polar configuration. More particularly, this is due to voltage efficiency, which may be defined as the ratio of the output voltage and the input voltage multiplied by the number of stages. For example, a 30 or 40 stage basic uni-polar voltage ladder will have a voltage efficiency of about 40 to 60%. For an input voltage of 15 kV, which is roughly the maximum voltage rating for most commercial components (e.g., capacitors and diodes) at reasonable sizes, the output voltage may be plotted against the number of stages. Cascading stages reduces the voltage efficiency. The output voltage converges to a given value, which is around 250 kV. Adding a relatively large number of stages may therefore not provide desired high operating voltages. The inability of such configurations to generate high voltages may further be attributed to the stray capacitance across the stages.

In order to generate a voltage of 400 kV with a uni-polar ladder (as opposed to a bi-polar design), for example, given the packaging size constraints of downhole equipment, the embodiments set forth herein provide for increased voltage efficiency through the use of one or more loading coils positioned at appropriate intermediate locations or positions in the ladder. A configuration in which a single boosting, or loading, coil was used in a uni-polar design for ion accelerators and television circuits is set forth in "The Cockcroft-Walton Voltage Multiplying Circuit", E. Everhart and P. Lorrain, 1953, The Review of Scientific Instruments, Vol. 24, 3, Mar. 1953. This configuration employed a single coil at the high voltage end of the voltage multiplier, boosting initial voltage efficiency from 50% to about 80%. With a classic Cockcroft-Walton ladder, the voltage efficiency is given by:

$$F = \frac{\tanh\left(2N\sqrt{\frac{C_S}{C}}\right)}{2N\sqrt{\frac{C_S}{C}}}, \quad (1)$$

where C is the ladder series capacitor, $C_s$ is the stray capacitance, and N is the number of voltage multiplication stages. With the above-noted single coil positioned at the end of a bi-polar voltage ladder, the efficiency becomes:

$$F = \frac{\tanh\left(N\sqrt{\frac{C_S}{C}}\right)}{N\sqrt{\frac{C_S}{C}}}. \quad (2)$$

By comparing equations with or without a loading coil, there is notably a factor of two difference. That is, the efficiency is the same as a uni-polar ladder without a loading coil, yet with two times fewer stages. A voltage distribution for this single, end-connected loading coil configuration is represented by plot line 63 in FIG. 5 (corresponding to an efficiency of approximately 78%), and a plot line 62 represents a uni-polar voltage ladder with no loading coil (corresponding to an efficiency of approximately 50%).

Even so, the voltage efficiency may be further improved by using one or more loading coils positioned between adjacent voltage multiplication stages in a voltage multiplication ladder. A first experiment was made with a first loading coil (0.4 H) at an end of the ladder, and a second loading coil (0.2 H) in the middle of the ladder, resulting in a voltage efficiency governed by the equation:

$$F = \frac{\tanh\left(\frac{N}{2}\sqrt{\frac{C_S}{C}}\right)}{\frac{N}{2}\sqrt{\frac{C_S}{C}}} \quad (3)$$

Figure 5:
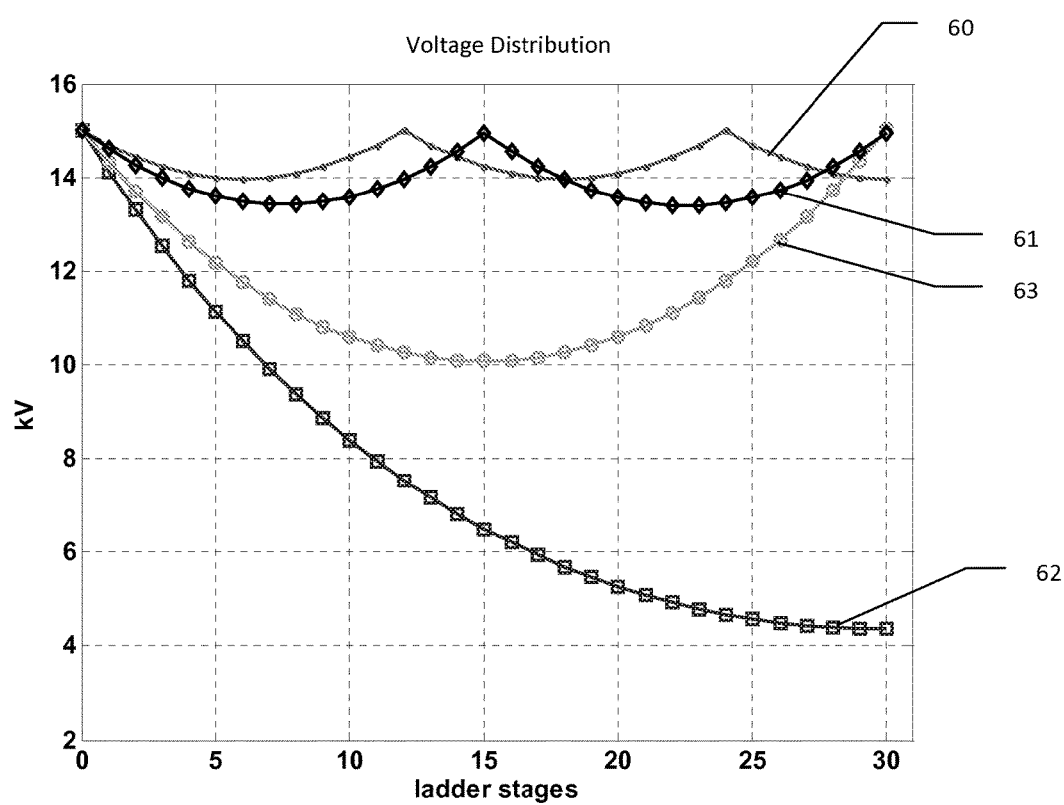
FIG. 5 is a plot comparing the voltage distribution along various uni-polar voltage ladder configurations with and without loading coils.

A voltage distribution for this configuration is represented by the plot line 61 in FIG. 5 (corresponding to an efficiency of approximately 93%). The voltage efficiency of this ladder is also improved over a ladder lacking loading coils, as it is equivalent to a ladder without coils yet with four times fewer stages.

Figure 4:
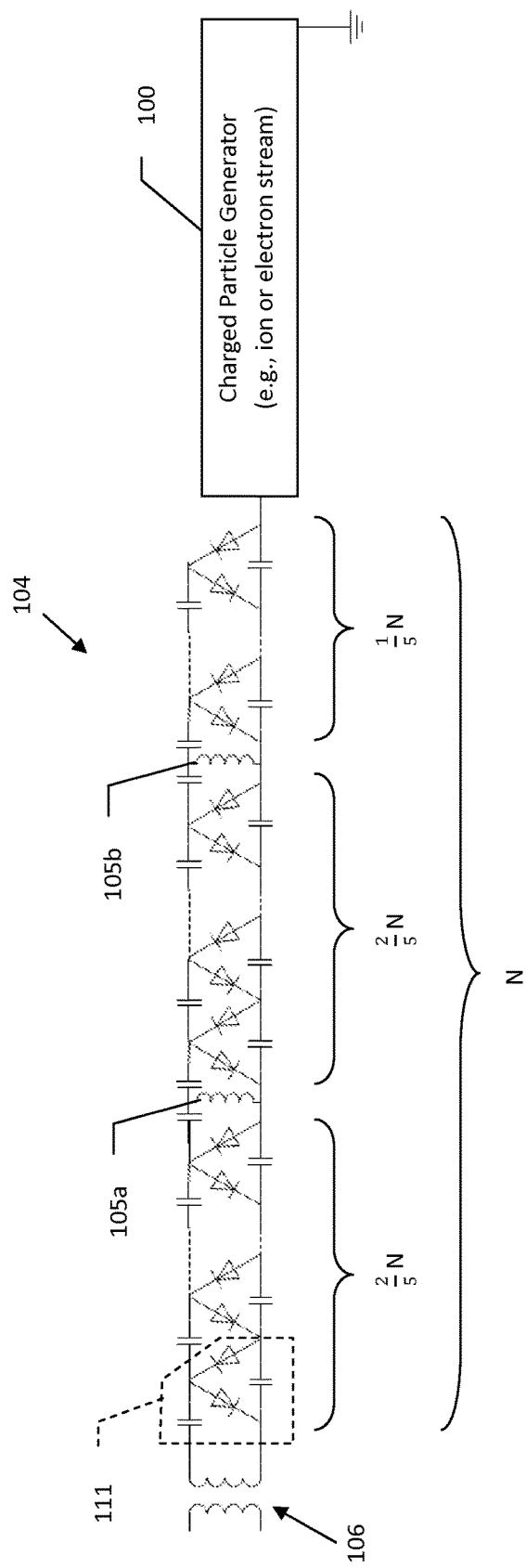
FIG. 4 is a schematic diagram of a uni-polar voltage ladder configuration which may be used with the radiation generator of FIG. 1.

Further experimentation proved that to have a desired voltage efficiency, the first and second coils 105a, 105b may be positioned two-fifths and four-fifths stage positions, respectively, down the length of the ladder 104 (as shown in FIG. 4). More particularly, with the first coil 105a and the second coil 105b, which are substantially identical to one another, respectively positioned at $2/5^{th}$ and $4/5^{th}$ along the length of the ladder 104, the voltage efficiency is governed by the equation:

$$F = \frac{\tanh\left(2\frac{N}{5}\sqrt{\frac{C_S}{C}}\right)}{2\frac{N}{5}\sqrt{\frac{C_S}{C}}} \quad (4)$$

From the above results it will be understood that a single intermediate loading coil 105 be used in some embodiments, and that the loading coils 105a, 105b may be located in positions other than the $2/5^{th}$ and $4/5^{th}$ positions.

A voltage distribution for this configuration is represented by the plot line 60 in FIG. 5 (which corresponds to an efficiency of approximately 96%). The efficiency is the same as a ladder without loading coils with five times less stages. For example, it is estimated that a ladder of forty stages with the two-coil configuration will have the same voltage efficiency as a ladder with no coil but with eight stages. At the optimum frequency, the input impedance is found to be:

$$Z_{in} = \frac{1}{i2\pi f \sqrt{CC_S} \tanh\left(2\frac{N}{5}\sqrt{\frac{C_S}{C}}\right)}. \quad (5)$$

with f being the optimum frequency. The impedance is then capacitive, with $$C_{eq} = \sqrt{CC_S} \tanh\left(2\frac{N}{5}\sqrt{\frac{C_S}{C}}\right). \quad (6)$$

The optimum coil values are:

$$L_2 = \frac{1}{2\omega^2 \sqrt{CC_S}} \times \frac{1}{\tanh\left(2\frac{N}{5}\sqrt{\frac{C_S}{C}}\right)} \text{ with } L_1 = L_2. \quad (7)$$

Hence, the above-described architecture allows for two coils of the same value to be used. The optimium frequency therefore will be equal to:

$$f_{opt} = \frac{1}{2\pi} \sqrt{\frac{1}{L\sqrt{CC_S}} \times \frac{1}{\tanh\left(2\frac{N}{5}\sqrt{\frac{C_S}{C}}\right)}}, \quad (8)$$

if:

$$N\sqrt{\frac{C_S}{C}} \ll 1, f_{opt} \approx \frac{1}{2\pi}\sqrt{\frac{5}{2NLC_S}}. \quad (9)$$

Figure 10:
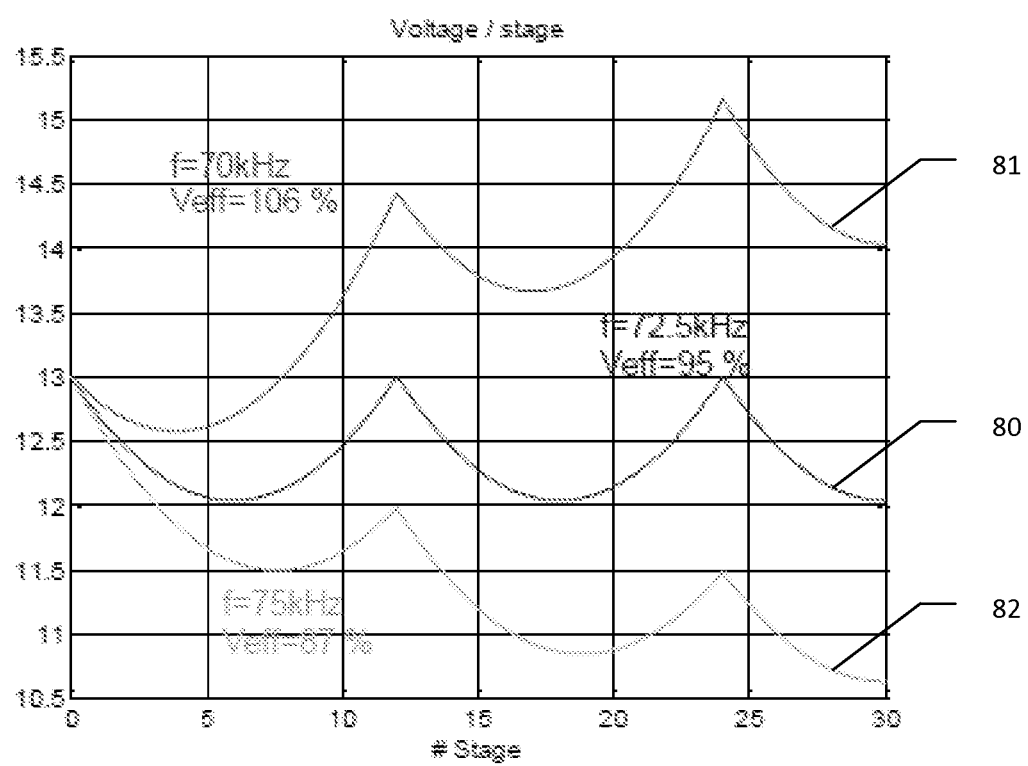
FIG. 10 is a graph illustrating voltage distribution based upon frequency variation for a radiation generator in an example test configuration.

At a first order approximation, the optimal frequency does not depend on the C value. The impact on the voltage distribution of a variation in the frequency may be seen in FIG. 10, in which a plot 80 represents the voltage distribution at an optimal frequency of 72.5 kHz with an efficiency of 95%. As represented by plot 81, if the frequency is too low (e.g., 70 kHz), the voltage efficiency is too high (106%), which means that some voltage multiplication stages will see a voltage higher than the input voltage. As represented by plot 82, if the frequency is too high (e.g., 75 kHz), the ladder does not work in its optimal mode, providing a voltage efficiency of 87%, as the voltage on the last stages is too low. However, it will be understood that an acceptable range of frequency variation (other than just the optimal frequency) may be used in some embodiments. An example configuration with a uni-polar voltage ladder and dual loading coils as described above was constructed and tested. The test configuration included the following:

- 30 voltage multiplication stages with 1 nF, X7R capacitors rated at 16 kV and 16 kV diodes;
- 2×0.2H coils, one being at $2/5^{th}$ of the ladder and the other one at $4/5^{th}$, with an operating frequency of 70 kHz;
- 6 PFA insulation sleeves (total thickness of 380 mil) and 3 layers of 20 mil FEP film;
- a 20 GΩ string of resistors (bleeder) at the end of the ladder to provide a measurement of the high voltage
- an X-ray tube; and
- a 40" long stainless steel pressure housing with a 3" OD (2.85" ID), pressurized with SF6 (around 120 psi).

The input voltage was measured with a 10 GΩ resistor string connected to the first stage of the ladder. The system was controlled with Labview. The test configuration was tested up to 400 kV and 40 µA and at elevated temperature. As can be seen by the results illustrated in FIG. 5, with loading coils in place in the uni-polar voltage ladder, particularly if placed in the optimized positions, substantially higher voltages are achieved for the same number, or fewer, of stages. This configuration may also be desirable not only in terms of the higher efficiency, but also since no coils are located on the ends of the voltage ladder, which may subject them to a greater risk of damage if arcing occurs.

Figure 6:
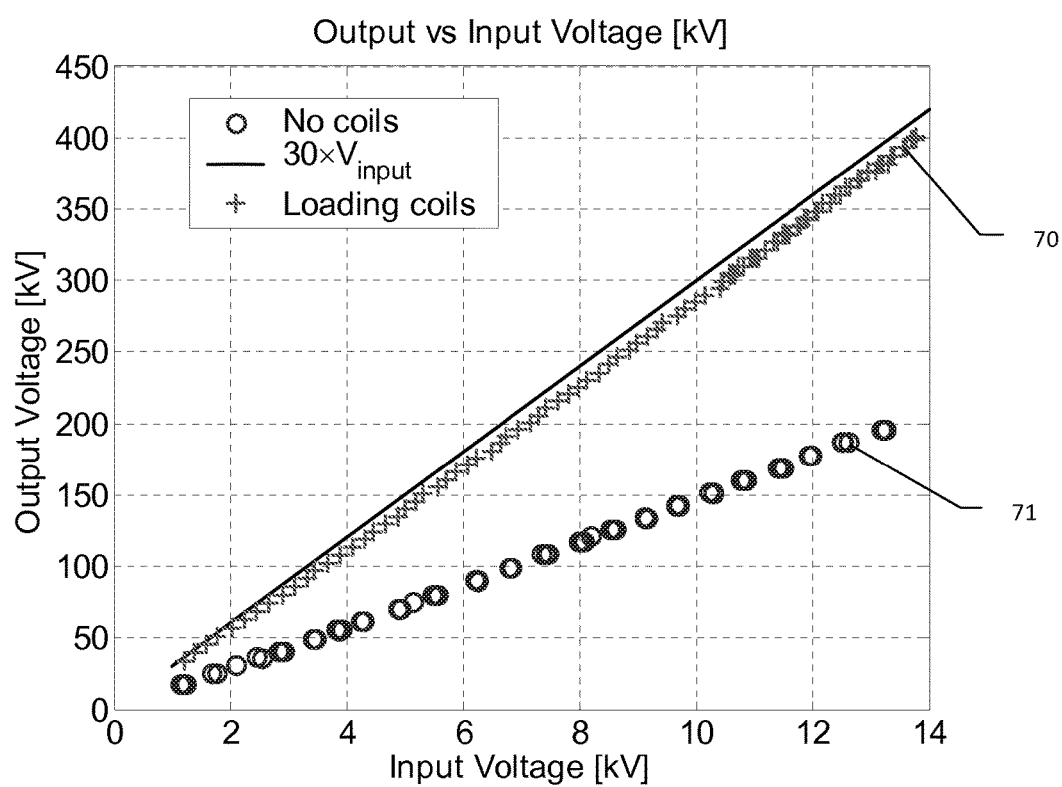
FIG. 6 is a plot of output voltage versus input voltage for the uni-polar voltage ladder configuration of FIG. 1, and for a uni-polar voltage ladder without added loading coils.
Figure 8:
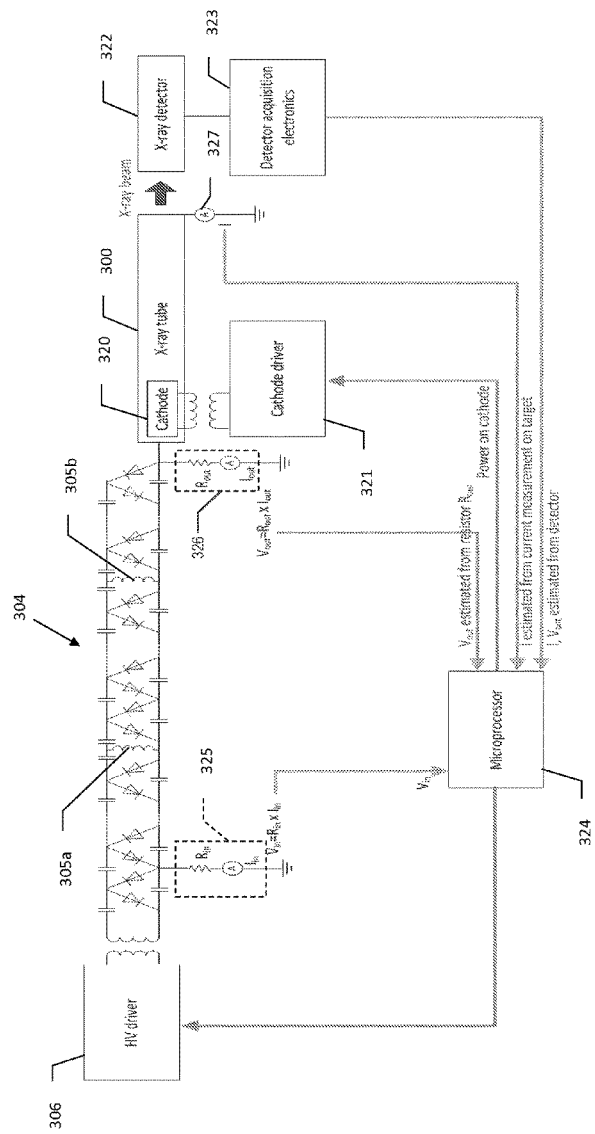
FIG. 8 is a schematic circuit diagram of an embodiment of a radiation generator and associated control circuitry.

With reference to FIG. 6, plots 70, 71 of output voltage versus input voltage, with and without loading coils added to a uni-polar voltage ladder, respectively, further illustrate the benefits of the loading coils 105a, 105b. This is helpful in terms of feedback and regulation. To stabilize the radiation generator, feedback loops on the input voltage, frequency and cathode drive may be used. One example radiation generator control configuration is shown in FIG. 8, in which the high voltage (HV) transformer or driver 306 is coupled to an input of the uni-polar voltage ladder 304, and the output of the uni-polar voltage ladder is coupled to a charged particle source 300 (here an X-ray tube including a cathode 320 coupled to an associated cathode driver 321). An X-ray detector 322 detects X-ray beams from the X-ray tube, and associated detector acquisition electronics 323 are coupled to the X-ray detector. A microprocessor 324 is coupled to the HV driver 306, an input voltage sensor 325, an output voltage sensor 326, the cathode driver 321, a cathode current sensor 327, and the detector acquisition electronics 323.

More particularly, the microprocessor 324 receives a measured input voltage $V_{in}$ to the ladder 304 from the input voltage sensor 325 (illustratively represented as a resistor $R_{in}$ and a current measurement $I_{in}$). Another input to the microprocessor 324 is an output voltage $V_{out}$ of the ladder 304 from the output voltage sensor 326 (illustratively represented as a resistor $R_{out}$ and a current measurement $I_{out}$). Other inputs to the microprocessor 324 include an target control current I from the cathode current sensor 327, as well as estimates of the current I and output voltage $V_{out}$ from the detector acquisition electronics 323. The microprocessor 324 may accordingly regulate the HV driver 306 and the cathode driver 321 to maintain constant values of the output voltage Vout, the current I, and a voltage efficiency value F, where $$F = \frac{V_{out}}{N \times V_{in}}.$$

In an example configuration, it may be desirable for the microprocessor 324 to maintain a voltage $V_{out}$=300 kV, a current I=100 µA, and a value of F=90%. As noted above, the value of the voltage Vout and current I may be estimated with resistors strings and/or with an X-ray detector measuring both the flux and the energy of the X-ray beam, for example. The voltage efficiency may be regulated to the desired value by adjusting the frequency of the voltage multiplication ladder 304 HV driver 306.

The voltage output $V_{out}$ is regulated to the desired value by adjusting the input voltage $V_{in}$. Measuring the input peak-to-peak voltage $V_{in}$ is performed to adjust the voltage efficiency with the frequency. Measuring a high voltage AC signal may be difficult as a result of cross-talk, for example. The input voltage $V_{in}$ may accordingly be approximated as the DC voltage on the first capacitor of the ladder's DC leg, which is theoretically very close to $V_{in}$. The output voltage $V_{out}$ may be estimated from a string of resistors or from a reference detector, as noted above. In parallel, the beam current is adjusted to the desired value by changing the cathode driver 321. By using loading coils 305a, 305b in the voltage ladder 304, the voltage efficiency may be boosted from approximately 50% to 95%, which makes a 400 kV single-ended ladder and grounded target generator feasible within the space constraints of a downhole tool.

The above-described uni-polar voltage ladder configurations may provide certain advantages over bipolar generator configurations in some embodiments. For example, this approach may help to reduce a risk of arcing, as there is no turn-around at the end of the ladders, and therefore no standoff to ground at the ends of the generator. Furthermore, high voltage may be confined in the middle of the generator with a ground at both ends. This in turn may reduce the risk of arcing or tracking on the insulating materials (by way of reference, see U.S. Pat. No. 7,564,948, which is also assigned to the present Assignee and is hereby incorporated herein in its entirety by reference). However, in some implementations, a bi-polar configuration with the same potential difference between the source and the target may have lower stresses on the insulation, since the maximum potential difference to ground may be as much as 50% lower, for example.

In addition, a risk of radiation damage may be reduced, as the target may be fully shielded, for example, by a tungsten collimator. Furthermore, thermal management of the power on the target may be relatively straightforward, since the target may be attached to a heat sink, for example. In addition, the mechanical design and assembly may be simplified, which may make it easier to maintain mechanical stability of the target, which is a consideration for the accuracy in the measurement (for example, formation density for X-ray measurements and porosity for neutron measurements).

Additionally, with a grounded target design, the distance between the point of emission of X-rays and the detector may be reduced, as the need for high voltage insulation on the target may be reduced (i.e., on the positive side of the X-ray tube). In particular, with a uni-polar configuration no voltage ladder needs to be positioned between the target and the detector, which may help reduce or eliminate high voltage turn-around, provide desired detector to target spacing, and additional room for the detector(s). Moreover, in some bipolar designs parasitic photons may reach the near detectors inside the pad. This may be mitigated by the above-described uni-polar configurations, which offer the ability to use backscatter-like detectors (e.g., PEx). Furthermore, the beam current (i.e., the flow of electrons in the tube hitting the target) may be measured directly.

Figure 7:
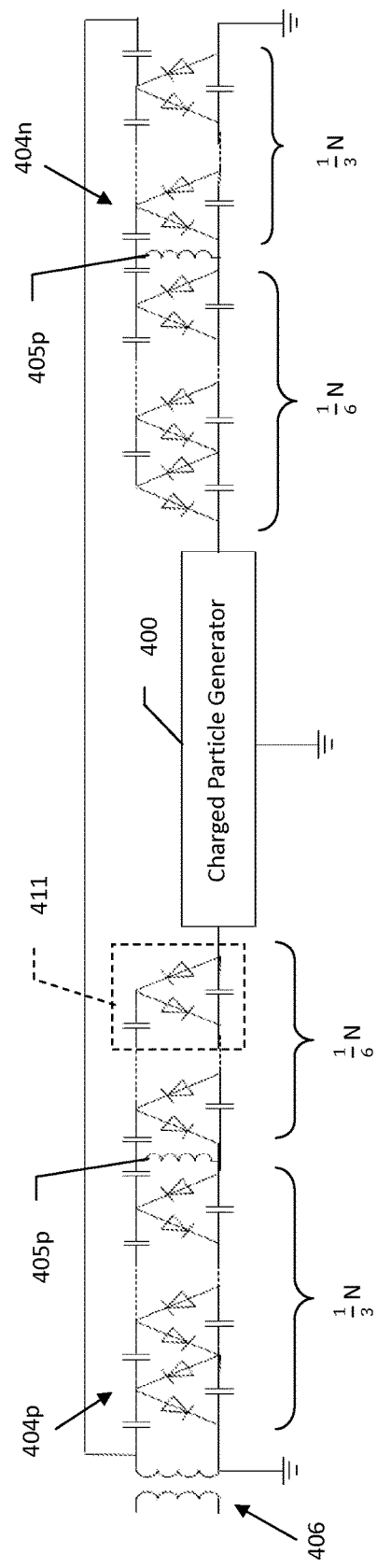
FIG. 7 is a schematic diagram of a bi-polar voltage ladder configuration which may be used with the radiation generator of FIG. 1.

However, in some embodiments it may be desirable to utilize a bi-polar voltage ladder configuration with a loading coil(s), as now described with reference to FIG. 7. In the illustrated example, the voltage ladder includes a positive voltage branch 404p and a negative voltage branch 404n, each of which includes a respective plurality of voltage multiplication stages 411, which are similar to those described above with reference to FIG. 4. Each of the branches 404p, 404n has a respective input coupled to a transformer or HV driver 406, and a respective output coupled to a charged particle generator 400 (e.g., an X-ray tube, ion generator, etc.) having a grounded target. In the illustrated example, loading coils 405p and 405n are coupled at respective intermediate positions along each of the positive voltage branch 404p and the negative voltage branch 404n.

More particularly, in the present example the intermediate positions are at one-third N, where N is the total number of the voltage multiplication stages 411 in both of the positive and negative voltage branches 404p, 404n, which has been determined to provide a desired voltage distribution similar to those discussed above for the uni-polar configurations. It may be shown that for the bi-polar configuration, the voltage efficiency is equal to:

$$F = \frac{\tan\left(2\frac{N}{3}\sqrt{\frac{C_S}{C}}\right)}{2\frac{N}{3}\sqrt{\frac{C_S}{C}}}. \tag{10}$$

By comparing equation (10) with equation (1) (i.e., no coils) or with equation (2) (i.e., a single, end-connected coil), it will be appreciated that the efficiency is improved and is equivalent to a ladder with approximately three times fewer stages.

Figure 11:
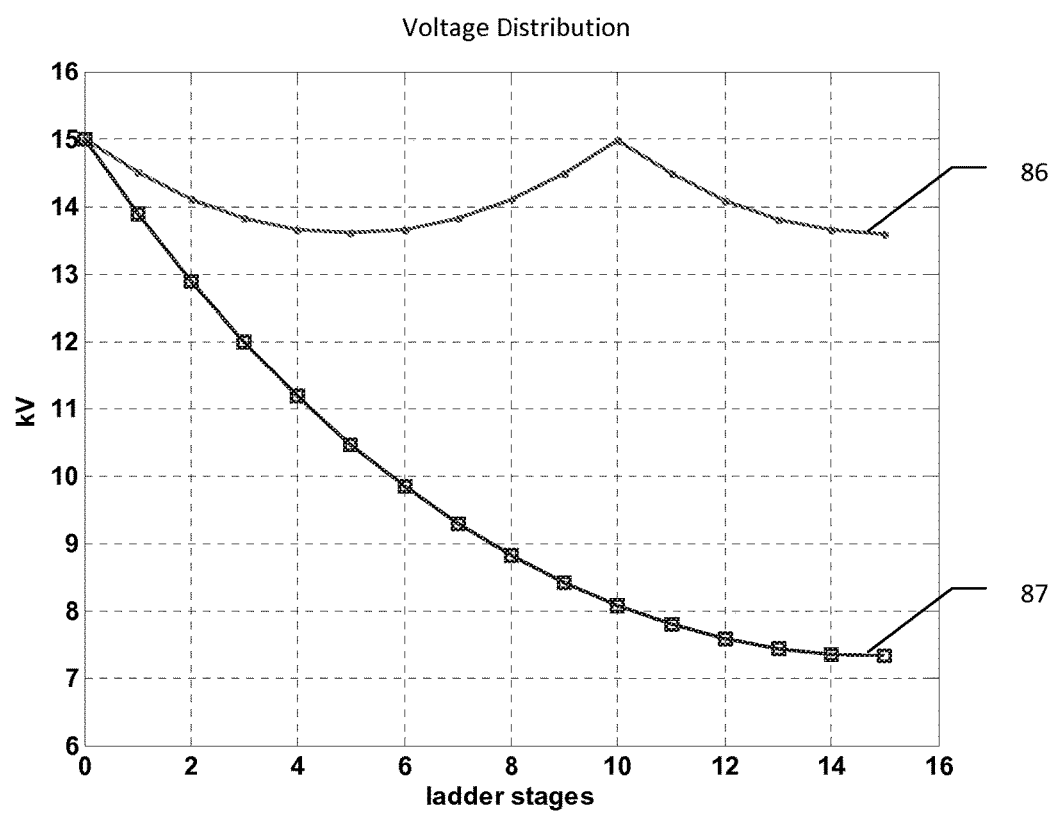
FIG. 11 is a plot comparing the voltage distribution along a bi-polar voltage ladder branch with a loading coil and a bi-polar voltage ladder branch with no loading coil.

The foregoing will be further understood with reference to FIG. 11, in which the voltage distribution of a bi-polar voltage ladder section having fifteen multiplication stages with a loading coil at the $\frac{1}{3}^{rd}$ position is shown by a plot line 86 (corresponding to an efficiency of approximately 95%), and the voltage distribution of a bi-polar ladder section also having fifteen multiplication but with no loading coil is shown by the plot 87 (corresponding to an efficiency of approximately 67%). However, as with the uni-polar configurations described above, different numbers of loadings coils and intermediate positions may be used in different embodiments.

It should be noted that to generate 400 kV with a bi-polar ladder, each of the positive and negative ladder sections has to generate +200 kV and −200 kV. The respective input voltage with fifteen stages would then be 14 kV with one coil at the $\frac{2}{3}^{rd}$ position (below 15 kV), and 20 kV with no coil (above what is actually achievable with current component technology in a confined space). Moreover, while the bi-polar ladder configuration may still utilize a ladder portion adjacent the anode (i.e., target), since the number of stages may be reduced as a result of the increased efficiency, this may still provide for increased space for the detector, as well as shorter distances between the target and the detector.

Figure 3:
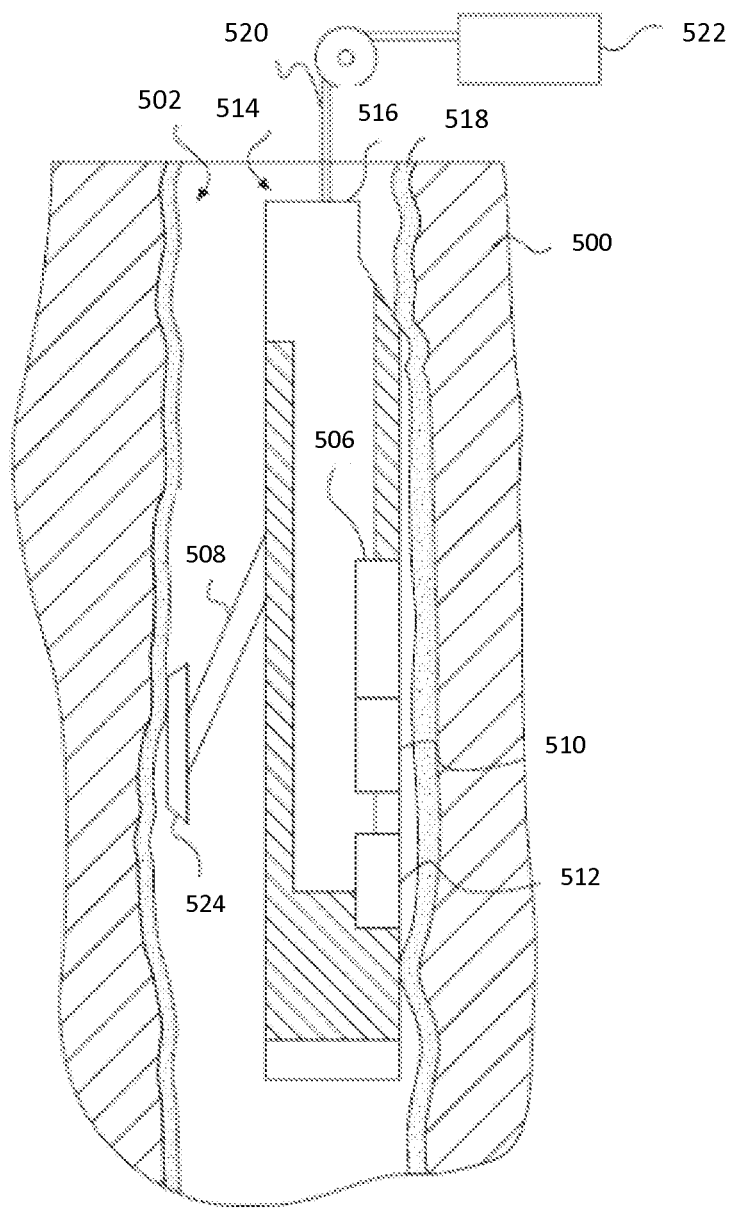
FIG. 3 is a schematic block diagram of a well-logging tool which may include a radiation generator as shown in FIG. 1.

Turning now to FIG. 3, an example application of the above-described radiation generators in a downhole well-logging tool 514 for determining the density and other properties of a formation 500 surrounding a borehole 502 is now described. As noted above, the tool 514 is positioned downhole to determine properties of the formation 500 using input radiation that is subsequently detected. In the illustrated embodiment, the tool 514 includes a sonde housing 516 that houses the components that are lowered into the borehole 502. In some embodiments, the sonde housing 516 may be a pad housing. Furthermore, a mandrel-type pressure housing may also be used for implementations such as wireline, slickline, CTD, TLC, etc. In another example configuration, the sonde housing 516 may be a collar to be carried by a Logging While Drilling (LWD) tool assembly or string, and the radiation generator may be carried or located in the chassis inside the collar, for example.

A radiation generator 512, such as those described above (e.g., X-ray, neutron, etc.) introduces radiation into the formation 500. The radiation is to some extent scattered from different depths in the formation 500, and the resultant radiation signal is detected by a short spaced detector 510 and a long spaced detector 506, for example, although other detector configurations may be used in various embodiments.

During the drilling process, the borehole may be filled with drilling mud. The liquid portion of the drilling mud flows into the formation 500, leaving behind a deposited layer of solid mud materials on the interior wall of the borehole in the form of mudcake 518. For reasons described below, it may be desirable to position the radiation generator 512 and detectors 506, 510 as close to the borehole wall as possible for taking measurements. Irregularities in the wall of the borehole may cause measurement degradation as the sonde housing 516 becomes longer, so it may be desirable to keep the entire tool 514 as short in length as possible. The sonde housing 516 is lowered into position and then secured against the borehole wall through the use of an arm 508 and a securing skid 524, for example. The tool 514, in one embodiment, is lowered into the borehole 502 via a wireline 520. Data is passed back to an analysis unit 522 for determination of formation properties. The tool 514 may be used downhole for wireline, logging-while-drilling (LWD), measurement-while-drilling (MWD), production logging, and permanent formation monitoring applications, as noted above, for example.

Figure 9:
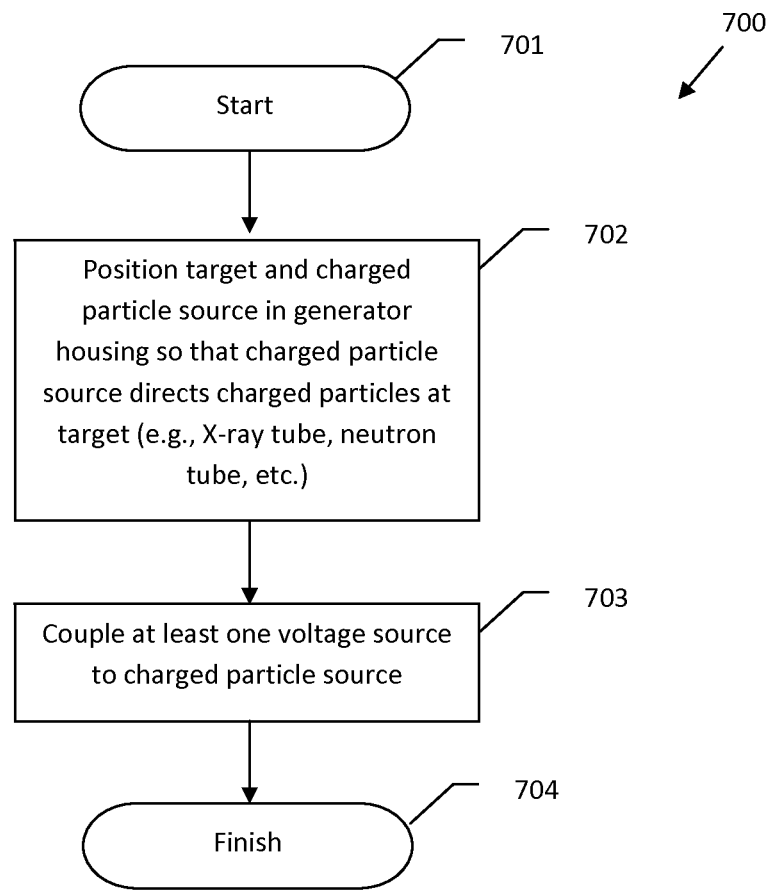
FIG. 9 is a flow diagram illustrating method aspects associated with making a radiation generator such as the one shown in FIG. 1.

A method of making radiation generators, such as those set forth above, is now described with reference to the flow diagram 700 of FIG. 9. Beginning at Block 701, a generator tube (e.g., an X-ray or neutron tube) is positioned in a generator housing 110 including a target and charged particle source, as described above, at Block 702. Additionally, at least one voltage source is coupled to the charged particle source, at Block 703. As noted above, the voltage source includes a voltage ladder 104 including a plurality of voltage multiplication stages coupled in a uni-polar (or bi-polar) configuration, and one or more loading coils 105 coupled at at least one intermediate position along the voltage ladder. The method concludes at Block 704.

As noted above, the above-described radiation generators may be used with both grounded target and floating target configurations. For most uni-polar neutron generator applications, the target is at a negative high voltage, while the ion source is virtually at ground. In X-ray tubes, it may be helpful to have the target at ground potential and the electron source at a high negative potential. In a bi-polar design, both the target and ion source may be floating, for example. In a minitron configuration, either the target or the ion source may be grounded, with the diodes in the voltage multiplication ladder oriented (or inverted) appropriately.

Many modifications and other embodiments will come to the mind of one skilled in the art having the benefit of the teachings presented in the foregoing descriptions and the associated drawings. Therefore, it is understood that various modifications and embodiments are intended to be included within the scope of the appended claims.

That which is claimed is:

1. A well-logging tool comprising:
   a sonde housing;
   a radiation generator carried by said sonde housing and comprising
      a generator housing,
      a target carried by said generator housing,
      a charged particle source carried by said generator housing to direct charged particles at said target, and
      at least one voltage source coupled to said charged particle source, said at least one voltage source comprising
         a voltage ladder comprising a plurality of voltage multiplication stages coupled in a bi-polar configuration,
         at least one loading coil coupled at at least one intermediate position along said voltage ladder,
         an operating frequency, and
         a voltage efficiency,
         wherein said operating frequency is configured to regulate said voltage efficiency to a value between eighty seven percent and one hundred and six percent; and
   at least one radiation detector carried by said sonde housing.

2. The well-logging tool of claim 1 wherein said voltage multiplication stages are arranged in a positive voltage branch and a negative voltage branch; and wherein said at least one loading coil comprises a respective loading coil coupled at respective intermediate positions along each of said positive voltage branch and said negative voltage branch.

3. The well-logging tool of claim 2 at least one of the intermediate positions is defined by one-third N, where N is a number of said voltage multiplication stages.

4. The well-logging tool of claim 1 wherein each of said voltage multiplication stages comprises at least one semiconductor diode.

5. The well-logging tool of claim 1 wherein said radiation generator further comprises:
   a voltage driver coupled to said voltage ladder;
   at least one voltage sensor coupled to said voltage ladder; and
   a processor to control said voltage driver based upon said at least one voltage sensor.

6. The well-logging tool of claim 1 wherein said charged particle source comprises an electron stream generator.

7. The well-logging tool of claim 1 wherein said charged particle source comprises an ion stream generator.

8. The well-logging tool of claim 1 wherein said voltage ladder comprises a Cockcroft-Walton voltage ladder.

9. The well-logging tool of claim 1 wherein said a sonde housing comprises a pad housing.

10. The well-logging tool of claim 1 wherein said a sonde housing comprises a mandrel housing.

11. The well-logging tool of claim 1 wherein said sonde housing comprises a collar to be carried by a Logging While Drilling (LWD) tool assembly; and wherein said collar comprises a chassis, and said radiation generator is carried in said chassis.

12. A radiation generator comprising:
   a generator housing;

a target carried by said generator housing;

a charged particle source carried by said generator housing to direct charged particles at said target; and at least one voltage source coupled to said charged particle source, said at least one voltage source comprising a voltage ladder comprising a plurality of voltage multiplication stages coupled in a bi-polar configuration, each multiplication stage comprising at least one semiconductor diode, at least one loading coil coupled at at least one intermediate position along said voltage ladder, an operating frequency, and a voltage efficiency, wherein said operating frequency is configured to regulate said voltage efficiency to a value between eighty seven percent and one hundred and six percent.

13. The radiation generator of claim 12 wherein said voltage multiplication stages are arranged in a positive voltage branch and a negative voltage branch; and wherein said at least one loading coil comprises a respective loading coil coupled at respective intermediate positions along each of said positive voltage branch and said negative voltage branch.

14. The radiation generator of claim 13 at least one of the intermediate positions is defined by one-third N, where N is a number of said voltage multiplication stages.

15. The radiation generator of claim 12 further comprising:

a voltage driver coupled to said voltage ladder;

at least one voltage sensor coupled to said voltage ladder; and a processor to control said voltage driver based upon said at least one voltage sensor.

16. The radiation generator of claim 12 wherein said charged particle source comprises an electron stream generator.

17. The radiation generator of claim 12 wherein said charged particle source comprises an ion stream generator.

18. The radiation generator of claim 12 wherein said voltage ladder comprises a Cockcroft-Walton voltage ladder.

19. A method for making a radiation generator comprising:

positioning a target and a charged particle source in a generator housing so that the charged particle source directs charged particles at the target; and coupling at least one voltage source to the charged particle source, the at least one voltage source comprising a voltage ladder comprising a plurality of voltage multiplication stages coupled in a bi-polar configuration, each multiplication stage comprising at least one semiconductor diode, at least one loading coil coupled at at least one intermediate position along the voltage ladder, an operating frequency, and a voltage efficiency, wherein said operating frequency is configured to regulate said voltage efficiency to a value between eighty seven percent and one hundred and six percent.

20. The method of claim 19 wherein the voltage multiplication stages are arranged in a positive voltage branch and a negative voltage branch; and wherein the at least one loading coil comprises a respective loading coil coupled at respective intermediate positions along each of the positive voltage branch and the negative voltage branch.

21. The method of claim 20 at least one of the intermediate positions is defined by one-third N, where N is a number of the voltage multiplication stages.

22. The method of claim 19 wherein the charged particle source comprises an electron stream generator.

23. The well-logging tool of claim 1, wherein said operating frequency is not equal to a resonant frequency of said voltage ladder.

* * * * *